United States Patent [19]

Mano

[11] Patent Number: 5,658,950

[45] Date of Patent: Aug. 19, 1997

[54] THERAPEUTIC AGENT FOR GLAUCOMA AND OCULAR HYPOTENSIVE AGENT

[75] Inventor: Tomiya Mano, Ibaraki, Japan

[73] Assignee: Mitsubishi Chemical Corporation, Tokyo, Japan

[21] Appl. No.: 458,687

[22] Filed: Jun. 2, 1995

[30] Foreign Application Priority Data

Jul. 6, 1994 [JP] Japan ...................... 6-154504

[51] Int. Cl.$^6$ .................................. A61K 31/19
[52] U.S. Cl. ............................. 514/570; 514/913
[58] Field of Search ....................... 514/570, 913

[56] References Cited

FOREIGN PATENT DOCUMENTS 0 072 942   3/1983   European Pat. Off. .

OTHER PUBLICATIONS

Database Biosis Biosciences Information Service, Philadelphia, PA, Acc. No. 11649054, 1995, H. Takenaka et al., "The effect of Anplag (Sarpogrelate HCl), novel selective 5–HT2 antagonist on intraocular pressure in glaucoma patients." *abstract* & Invest. Ophthalmol Visual Sci., vol. 36, No. 4, 1995, p. 734.

*Primary Examiner*—Zohreh Fay
*Attorney, Agent, or Firm*—Wenderoth, Lind & Ponack

[57] ABSTRACT

The present invention provides a novel drug for treating glaucoma.

The present invention relates to a therapeutic agent for glaucoma and an ocular hypotensive agent, which comprise an aminoalkoxybibenzyl represented by the formula (I):

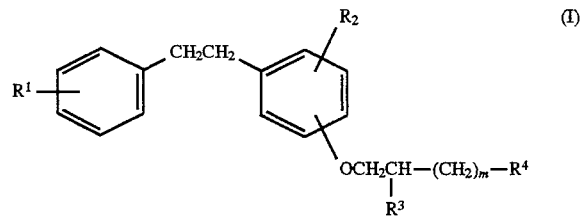

wherein $R^1$ represents a hydrogen atom, a $C_1$–$C_5$ alkoxy group, etc.; $R^2$ represents a hydrogen atom, a halogen atom, etc.; $R^3$ represents a hydrogen atom, a hydroxyl group, —O—CO—$(CH_2)_l$—COOH (wherein l is an integer of 1 to 3), etc.; and $R^4$ represents —$NR^5R^6$ (wherein $R^5$ and $R^6$ independently represent a hydrogen atom or a $C_1$–$C_8$ alkyl group), etc.

or a salt thereof as an active ingredient.

14 Claims, No Drawings

THERAPEUTIC AGENT FOR GLAUCOMA AND OCULAR HYPOTENSIVE AGENT

BACKGROUND OF THE INVENTION

1. Field of the Invention

The present invention relates to a therapeutic agent for ophthalmic disease comprising aminoalkoxybibenzyls or a salt thereof as an active ingredient. More particularly, it relates to a therapeutic agent for glaucoma, and an ocular hypotensive agent.

2. Description of the Related Art

Glaucoma is considered to be a group of diseases wherein the entoptic tissue (particularly function of optic nerve cell) is damaged from lesions causing an abnormal ocular tension. Normally, the principal factors of the mechanism causing lesions are considered to be ischemic symptoms and disorder of optic nerve axonal flow due to mechanical compression in the lamina cribrosa caused by an increase in ocular tension. However, the mechanism of the increase in ocular tension is not clear at present. Further, in Japanese Patent Publication No. 13427/1988, the structure of aminoalkoxybibenzyls and a salt thereof is described. It is also described that they has an effect to increase an anticoagulant action and a prostaglandin $I_2$ action.

The significance of glaucoma as degenerative diseases has been increasing in advanced nations which have already entered in an ultra aging society, and good remedies for glaucoma have been requested still now.

SUMMARY OF THE INVENTION

In order to solve the above problems, the present inventors have studied intensively. As a result, it has been found that aminoalkoxybibenzyls having a specific structure or a salt thereof has an ocular tension reducing action and is useful for treating glaucoma, and the present invention has been accomplished.

The main object of the present invention is to provide a therapeutic agent for glaucoma and an ocular hypotensive agent.

This object as well as other objects and advantages of the present invention will become apparent to those skilled in the art from the following description.

The present invention provides a therapeutic agent for glaucoma and an ocular hypotensive agent, which comprise an aminoalkoxybibenzyl represented by the general formula (I):

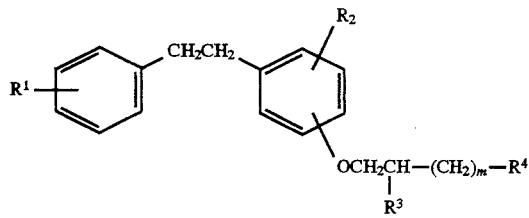

wherein $R^1$ represents a hydrogen atom, a halogen atom, a $C_1$–$C_5$ alkoxy group or a $C_2$–$C_6$ dialkylamino group;

$R^2$ represents a hydrogen atom, a halogen atom or a $C_1$–$C_5$ alkoxy group;

$R^3$ represents a hydrogen atom, a hydroxyl group, —O—$(CH_2)_n$—COOH (wherein n is an integer of 1 to 5) or —O—CO—$(CH_2)_l$—COOH (wherein l is an integer of 1 to 3);

$R^4$ represents a group of the general formula:

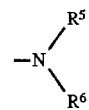

wherein $R^5$ and $R^6$ independently represent a hydrogen atom or a $C_1$–$C_8$ alkyl group, or a group of the general formula:

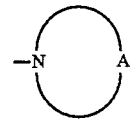

wherein A is a $C_3$–$C_5$ alkylene group which may be substituted with a carboxyl group; and m is an integer of 0 to 5, or a salt thereof as an active ingredient.

DETAILED DESCRIPTION OF THE INVENTION

The definition in the above formula will be explained in detail hereinafter. $R^1$ represents a hydrogen atom, a halogen atom (e.g. a chlorine atom, a fluorine atom, etc.), a $C_1$–$C_5$ alkoxy group (e.g. a methoxy group, an ethoxy group, a butoxy group, etc.) or a $C_2$–$C_6$ dialkylamino group (e.g. a dimethylamino group, a diethylamino group, a methylethylamino group, etc.); $R^2$ is a hydrogen atom, a halogen atom (e.g. a chlorine atom, a fluorine atom, etc.) or a $C_1$–$C_5$ alkoxy group (e.g. a methoxy group, an ethoxy group, a butoxy group, etc.);

$R^3$ represents a hydrogen atom, a hydroxyl group, —O—$(CH_2)_n$—COOH (wherein n is an integer of 1 to 5) such as —O—$(CH_2)_2$—COOH, —O—$(CH_2)_3$—COOH, etc. or —O—CO—$(CH_2)_l$—COOH (wherein l is an integer of 1 to 3) such as —O—CO—$(CH_2)_2$—COOH, —O—CO—$(CH_2)_3$—COOH, etc.;

$R^4$ represents a group of the general formula:

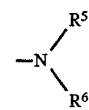

wherein $R^5$ and $R_6$ independently represent a hydrogen atom or a $C_1$–$C_8$ alkyl group such as a methyl group, a butyl group, hexyl group, a heptyl group, etc., such as an amino group, a methylamino group, an ethylamino group, a butylamino group, a hexylamino group, a heptylamino group, a dimethylamino group, a diethylamino group, a methylethylamino group, etc., or a group of the general formula:

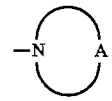

wherein A represents a $C_3$–$C_5$ alkylene group which may be substituted with a carboxyl group, such as

etc.; and m is an integer of 0 to 5.

In the present invention, the aminoalkoxy group of the formula:

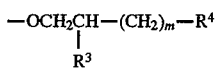

is preferably positioned on the 2-position in the aminoalkoxybibenzyl of the formula (I). Further, $R^1$ is preferably a hydrogen atom, a $C_1-C_5$ alkoxy group or a $C_2-C_6$ dialkylamino group. $R^2$ is preferably a hydrogen atom. $R^4$ is preferably a group of the formula:

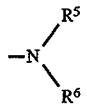

wherein at least one of $R^5$ and $R^6$ is a $C_1-C_8$ alkyl group, or a group of the formula:

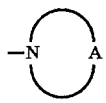

wherein A is a methylene group.

m is preferably an integer of 0 to 2.

Further, pharmaceutically acceptable acid addition salts of the above compounds may also be included in the scope of the present invention.

Examples of the acid addition salt include addition salts of acids such as hydrochloric acid, hydrobromic acid, sulfuric acid, phosphoric acid, nitric acid, acetic acid, succinic acid, adipic acid, propionic acid, tartaric acid, maleic acid, oxalic acid, citric acid, benzoic acid, toluenesulfonic acid, methanesulfonic acid and the like.

Among aminoalkoxybibenzyls to be used in the present invention, examples of the most preferred compound include the following compounds:

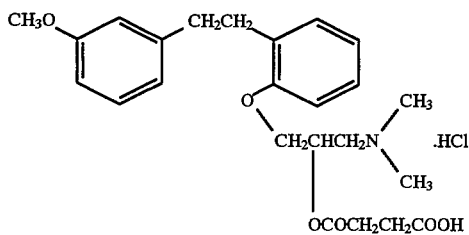

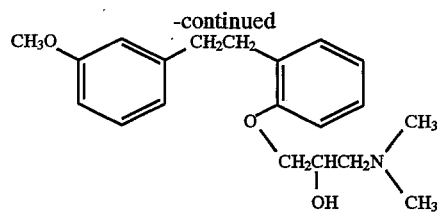

or its salts.

The above aminoalkoxybibenzyls to be used in the present invention are known compounds and can be easily synthesized, for example, by the method described in Japanese Patent Publication No. 13427/1988.

The therapeutic agents of the present invention may be oral agents, injections, eye drops, ointments and the like. For oral agents, they may be tablets, capsules, powders, liquid preparations, elixirs and the like. Non-toxic solids or liquids can be contained in the therapeutic agent as a pharmaceutically acceptable carrier.

When the solid carrier is used, there is exemplified a conventional gelatin-type capsule. Further, an active ingredient can be used with or without auxiliaries to form a tablet or a powder packing.

These capsules, tablets and powders contain normally 5 to 95% by weight, preferably 25 to 90% by weight, of the active ingredient.

That is, these dosage forms can contain 5 to 500 mg, preferably 25 to 250 mg, of the active ingredient per dose.

As the liquid carrier, there can be used water, oils originated from animals/vegetables (e.g. petroleum, peanut oil, soybean oil, mineral oil, sesame oil, etc.) or synthetic oils.

As the liquid carrier, there can be suitably used saline, dextrose or similar sucrose solution, glycols (e.g. propylene glycol, polyethylene glycol, etc.) and the like. Particularly, an injection using saline contains normally 0.5 to 20% by weight, preferably 1 to 10% by weight, of the active ingredient.

In case of the liquid preparation for oral administration, a suspension or syrup containing 0.5 to 10% by weight of the active ingredient is preferred. In this case, aqueous excipients (e.g. flavor, syrup, pharmaceutical micelle, etc.) may be used as the carrier.

In order to prepare the eye drop, various additives described below may be appropriately added to a solution obtained by dissolving aminoalkoxybibenzyls represented by the formula (I) in water.

As a buffer, for example, there can be used phosphate buffer, borate buffer, tartrate buffer, acetate buffer, amino acid and the like.

As an isotonicity, for example, there can be used sugars (e.g. sorbitol, glucose, mannitol, etc.), polyhydric alcohols (e.g. glycerine, propylene glycol, etc.), salts (e.g. sodium chloride, etc.) and the like.

As an antiseptic, for example, there can be used quaternary ammonium salts (e.g. benzalkonium chloride, benzethonium chloride, etc.), paraoxybenzoates (e.g. methyl paraoxybenzoate, ethyl paraoxybenzoate, etc.), benzyl alcohol, phenethyl alcohol, sorbic acid and a salt thereof, thimerosal, chlorobutanol and the like.

As a viscous agent, for example, there can be used hydroxyethyl cellulose, hydroxypropyl cellulose, methyl cellulose, hydroxypropylmethyl cellulose, carboxymethyl cellulose and a salt thereof.

An ointment can be prepared by homogeneously mixing an aminoalkoxybibenzyl of the general formula (I) with a suitable base (e.g. vaseline, etc.) and optionally adding preservatives, stabilizers or other suitable additives.

The dose of aminoalkoxybenzyls of the formula (I) contained in the preparations of the present invention varies depending upon the patient's age, weight and symptoms, severity of diseases and the like, and it should be finally decided by the clinical doctor. It is administered with a daily dose of normally 0.5 to 50 mg/kg, preferably 1 to 30 mg/kg, for one or more days. When the preparation of the present invention is the oral agent, 50 mg or 100 mg of the aminoalkoxybibenzyl are contained in the unit dosage form. For example, it is normally administered 1 to 3 times per day with a dose of 100 mg/time. In the case of the injection, the aminoalkoxybibenzyl is normally administered 1 to 4 times per day with a dose of 10 to 30 mg/time. In the case of the eye drop, an eye drop containing the amonoalkoxybibenzyl in a concentration of 0.1 to 1% is prepared and the eye drop is administered. 1 to 4 times per day.

The preparations of the present invention can be widely applied in the ophthalmic field on the basis of an ocular hypotensive action of the aminoalkoxybibenzyls. For example, the preparations containing the aminoalkoxybibenzyls as the active ingredient of the present invention are useful for preventing or treating glaucoma, ocular hypertension and the like. Further, glaucoma include high tension glaucoma and low tension glaucoma (normal tension glaucoma) wherein glaucomatous abnormalities of optic disk and glaucomatous abnormalities of the visual field are recognized while exhibiting normal ocular tension. The preparations of the present invention are effective for the both and is particularly effective for high tension glaucoma.

The following Examples further illustrate the present invention in detail but are not to be construed to limit the scope thereof.

EXAMPLE 1

To patients having an ocular tension of more than 21 mmHg, a preparation containing 100 mg of salpoglelate hydrochloride (chemical name: (±)-1-[o-[2-(m-methoxyphenyl)ethyl]phenoxy]-3-(dimethylamino)-2-propyl hydrogensuccinate hydrochloride) was administered orally 3 times per day for 1 to 3 weeks to examine oral hypotensive action for the salpoglelate hydrochloride.

The results are shown in Table 1, below. In Table 1, the value of ocular tension immediately before administration of this preparation, the value after administration for a predetermined period and the value after a predetermined period has passed since the completion of the administration of this preparation are shown in the items of "before administration", "during administration" and "after completion of administration", respectively.

TABLE 1

| | | | | | Ocular tension (mmHg) | | | |
| --- | --- | --- | --- | --- | --- | --- | --- | --- |
| No. | Initial | Sex | Age | | Before administration | During administration | | After completion of administration |
| 1 | S.H. | F | 70 | Date | 3/1 | 3/8 | | 3/18 | 3/25 |
| | | | | Right | 26 | 21 | | 21 | 22 |
| | | | | Left | 23 | 21 | | 19 | 19 |
| 2 | N.N. | M | 68 | Date | 2/15 | 2/22 | | 3/22 | 4/5 |
| | | | | Right | 26 | 18 | | 21 | 17 |
| | | | | Left | 18 | 16 | | 15 | 15 |
| 3 | T.K. | M | 50 | Date | 2/18 | 2/22 | | 3/22 | |
| | | | | Right | 20 | 15 | | 20 | |
| | | | | Left | 18 | 14 | | 18 | |
| 4 | D.T. | M | 54 | Date | 2/14 | 2/28 | | 3/28 | |
| | | | | Right | 28 | 22 | | 33 | |
| | | | | Left | 27 | 22 | | 25 | |
| 5 | R.A. | F | 23 | Date | 2/15 | 3/1 | | 4/5 | |
| | | | | Right | 28 | 24 | | 23 | |
| | | | | Left | 26 | 23 | | 25 | |
| 6 | K.N. | F | 48 | Date | 2/22 | 3/1 | | 3/11 | 3/25 |
| | | | | Right | 30 | 23 | | 27 | 27 |
| | | | | Left | 30 | 22 | | 25 | 24 |
| 7 | T.M. | M | 51 | Date | 2/22 | 3/1 | | 4/5 | |
| | | | | Right | 23 | 19 | | 18 | |
| | | | | Left | 23 | 18 | | 17 | |
| 8 | K.M. | F | 58 | Date | 2/22 | 3/1 | | 4/5 | |
| | | | | Right | 25 | 22 | | 24 | |
| | | | | Left | 23 | 22 | | 21 | |
| 9 | Y.M. | F | 72 | Date | 2/22 | 3/1 | 3/22 | | |
| | | | | Right | 22 | 24 | 18 | | |
| | | | | Left | 16 | 18 | 19 | | |
| 10 | S.T. | F | 68 | Date | 2/4 | 2/18 | 3/4 | 3/18 | 4/1 |
| | | | | Right | 28 | 25 | 26 | 28 | 27 |
| | | | | Left | 25 | 25 | 26 | 27 | 25 |
| 11 | K.T. | F | 65 | Date | 2/22 | 3/1 | | 3/15 | 4/5 |
| | | | | Right | 26 | 22 | | 26 | 28 |
| | | | | Left | 26 | 22 | | 22 | 28 |
| 12 | M.N. | F | 65 | Date | 2/4 | 2/15 | 3/4 | | |
| | | | | Right | 24 | 17 | 21 | | |
| | | | | Left | 20 | 18 | 17 | | |
| 13 | K.K. | F | 25 | Date | 2/22 | 3/1 | | 3/22 | |
| | | | | Right | 25 | 20 | | 21 | |
| | | | | Left | 15 | 13 | | 14 | |
| 14 | H.N. | M | 69 | Date | 2/25 | 3/4 | | 4/1 | |
| | | | | Right | 23 | 22 | | 24 | |
| | | | | Left | 21 | 19 | | 22 | |

TABLE 1-continued

| | | | | | Ocular tension (mmHg) | | | |
| | | | | | Before | During | After completion of | |
| No. | Initial | Sex | Age | | administration | administration | administration | |
|---|---|---|---|---|---|---|---|---|
| 15 | T.I. | M | 63 | Date | 3/1 | 3/8 | 3/15 | 3/29 |
| | | | | Right | 26 | 19 | 19 | 16 |
| | | | | Left | 26 | 19 | 19 | 16 |
| 16 | T.S. | F | 62 | Date | 3/1 | 3/8 | 3/15 | 3/29 |
| | | | | Right | 24 | 21 | 21 | 20 |
| | | | | Left | 26 | 23 | 23 | 20 |
| 17 | E.K. | M | 61 | Date | 2/18 | 2/25 | | |
| | | | | Right | 18 | 16 | | |
| | | | | Left | 28 | 23 | | |
| 18 | K.T. | F | 45 | Date | 3/25 | 4/1 | | |
| | | | | Right | 26 | 23 | | |
| | | | | Left | 26 | 23 | | |
| 19 | T.S. | M | 64 | Date | 3/10 | 3/17 | | |
| | | | | Right | 21 | 21 | | |
| | | | | Left | 16 | 13 | | |
| 20 | R.O. | M | 78 | Date | 2/22 | 3/1 | 3/7 | 3/22 |
| | | | | Right | 28 | 28 | 28 | 25 |
| | | | | Left | 22 | 22 | 22 | 22 |
| 21 | Z.I. | M | 59 | Date | 2/18 | 3/1 | 3/8 | 3/29 |
| | | | | Right | 38 | 16 | 16 | 13 |
| | | | | Left | 29 | 19 | 18 | 14 |
| 22 | K.A. | M | 50 | Date | 2/9 | 2/15 | | |
| | | | | Right | 17 | 17 | | |
| | | | | Left | 29 | 44 | | |
| 23 | M.E. | M | 64 | Date | 2/15 | 2/16 | 2/25 | 3/4 | 3/11 |
| | | | | Right | 17 | 17 | 16 | 19 | 20 |
| | | | | Left | 23 | 35 | 21 | 19 | 20 |
| 24 | T.N. | M | 55. | Date | 3/15 | 3/22 | | |
| | | | | Right | 21 | 19 | | |
| | | | | Left | 21 | 19 | | |
| 25 | T.T. | M | 70 | Date | 3/15 | 3/22 | 4/5 | |
| | | | | Right | 24 | 17 | 16 | |
| | | | | Left | 21 | 17 | 17 | |
| 26 | M.I. | F | 57 | Date | 3/15 | 3/22 | 4/5 | |
| | | | | Right | 33 | 27 | 27 | |
| | | | | Left | 32 | 27 | 26 | |
| 27 | H.I. | M | 56 | Date | 3/1 | 3/5 | 3/8 | 4/5 |
| | | | | Right | 21 | 23 | 19 | 21 |
| | | | | Left | 29 | 30 | 22 | 20 |
| 28 | T.T. | M | 63 | Date | 3/11 | 3/14 | 3/18 | 3/25 |
| | | | | Right | 40 | 29 | 29 | 15 |
| | | | | Left | 19 | 17 | 16 | 14 |

Ocular tension was not changed in five cases (10, 14, 20, 23 and 24) and the ocular tension of the case 22 was increased. However, the ocular tension was decreased by 3 mm Hg or more in other cases. It can be judged from these data that salpoglelate hydrochloride has the ocular hypotensive action. Further, the above data shows that the ocular hypotensive is maintained even if the administration of salpoglelate chloride is stopped. Accordingly, salpoglelate hydrochloride is useful as the ocular hypotensive agent.

Furthermore, it is a good therapeutic means for glaucoma to decrease the ocular tension so that salpoglelate hydrochloride is considered to be useful as a therapeutic agent for glaucoma, particularly glaucoma accompanied with a increase in ocular tension.

Further, particularly significant side effects were not recognized in all cases.

What is claimed is:

1. A method for treating glaucoma, comprising administering to a patient in need of said treatment a therapeutically effective amount of a pharmaceutical composition comprising an aminoalkoxybibenzyl represented by the formula (I):

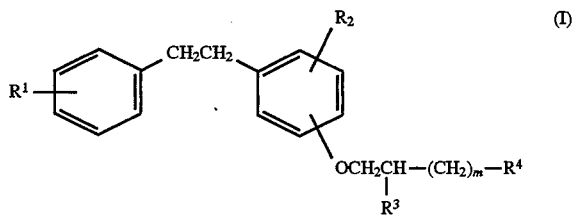

(I)

wherein $R^1$ represents a hydrogen atom, a halogen atom, a $C_1$–$C_5$ alkoxy group or a $C_2$–$C_6$ dialkylamino group;

$R^2$ represents a hydrogen atom, a halogen atom or a $C_1$–$C_5$ alkoxy group;

$R^3$ represents a hydrogen atom, a hydroxyl group, —O—$(CH_2)_n$—COOH (wherein n is an integer of 1 to 5) or —O—CO—$(CH_2)_l$—COOH (wherein l is an integer of 1 to 3);

9

$R^4$ represents a group of the general formula:

$$-N\begin{matrix}R^5\\ \\R^6\end{matrix}$$

wherein $R^5$ and $R^6$ independently represent a hydrogen atom or a $C_1$–$C_8$ alkyl group, or a group of the general formula:

$$-N\underset{\phantom{.}}{\bigcirc}A$$

wherein A represents a $C_3$–$C_5$ alkylene group which may be substituted with a carboxyl group; and m is an integer of 0 to 5, or a salt thereof as an active ingredient and a pharmaceutically acceptable carrier.

2. The method according to claim 1, wherein the pharmaceutical composition comprises a salt of an aminoalkoxybibenzyl represented by the formula:

[Structure: CH₃O-phenyl-CH₂CH₂-phenyl-O-CH₂CHCH₂N(CH₃)(CH₃)·HCl with OCOCH₂CH₂COOH]

as the active ingredient.

3. The method according claim 1, wherein the pharmaceutical composition comprises an aminoalkoxybibenzyl represented by the formula:

[Structure: CH₃O-phenyl-CH₂CH₂-phenyl-O-CH₂CHCH₂N(CH₃)(CH₃) with OH]

or a salt thereof as the active ingredient.

4. The method according to any one of claims 1 to 3, wherein the pharmaceutical composition is administered orally.

5. The method according to any one of claims 1 to 3, wherein the pharmaceutical composition is administered by injection.

6. The method according to any one of claims 1 to 3, wherein the pharmaceutical composition is administered in the form of an eye drop.

7. The method according to any one of claims 1 to 3, wherein the pharmaceutical composition is administered in the form of an ointment.

8. A method for treating ocular hypertension, comprising administering to a patient in need of said treatment a therapeutically effective amount of a pharmaceutical composition comprising an aminoalkoxybibenzyl represented by the formula (I):

[Structure (I): $R^1$-phenyl-CH₂CH₂-phenyl-$R^2$ with OCH₂CH($R^3$)-(CH₂)$_m$-$R^4$]

wherein $R^1$ represents a hydrogen atom, a halogen atom, a $C_1$–$C_5$ alkoxy group or a $C_2$–$C_6$ dialkylamino group;

$R^2$ represents a hydrogen atom, a halogen atom or a $C_1$–$C_5$ alkoxy group;

$R^3$ represents a hydrogen atom, a hydroxyl group, —O—(CH$_2$)$_n$—COOH (wherein n is an integer of 1 to 5) or —O—CO—(CH$_2$)$_l$—COOH (wherein $l$ is an integer of 1 to 3);

$R^4$ represents a group of the general formula:

$$-N\begin{matrix}R^5\\ \\R^6\end{matrix}$$

wherein $R^5$ and $R^6$ independently represent a hydrogen atom or a $C_1$–$C_8$ alkyl group, or a group of the general formula:

$$-N\underset{\phantom{.}}{\bigcirc}A$$

wherein A represents a $C_3$–$C_5$ alkylene group which may be substituted with a carboxyl group; and m is an integer of 0 to 5, or a salt thereof as an active ingredient and a pharmaceutically acceptable carrier.

9. The method according to claim 8, wherein the pharmaceutical composition comprises a salt of an aminoalkoxybibenzyl represented by the formula:

[Structure: CH₃O-phenyl-CH₂CH₂-phenyl-O-CH₂CHCH₂N(CH₃)(CH₃)·HCl with OCOCH₂CH₂COOH]

as the active ingredient.

10. The method according to claim 8, wherein the pharmaceutical composition comprises an aminoalkoxybibenzyl represented by the formula:

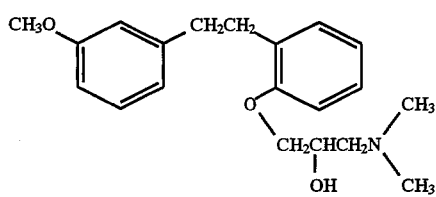

or a salt thereof as the active ingredient.

11. The method according to any one of claims 8 to 10, wherein the pharmaceutical composition is administered orally.

12. The method according to any one of claims 8 to 10, wherein the pharmaceutical composition is administered by injection.

13. The method according to any one of claims 8 to 10, wherein the pharmaceutical composition is administered in the form of an eye drop.

14. The method according to any one of claims 8 to 10, wherein the pharmaceutical composition is administered in the form of an ointment.

* * * * *